US008182732B2

United States Patent
Ukegawa et al.

(10) Patent No.: US 8,182,732 B2
(45) Date of Patent: May 22, 2012

(54) STRETCHABLE COMPOSITE SHEET AND PROCESS FOR FORMING THE SAME WITH A PLURALITY OF GATHERS

(75) Inventors: Kazuo Ukegawa, Kagawa-ken (JP); Masato Isono, Kagawa-ken (JP); Hiroaki Kamio, Kagawa-ken (JP); Toru Oba, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 1078 days.

(21) Appl. No.: 10/970,535

(22) Filed: Oct. 21, 2004

(65) Prior Publication Data

US 2005/0084656 A1    Apr. 21, 2005

Related U.S. Application Data

(62) Division of application No. 10/165,228, filed on Jun. 7, 2002, now Pat. No. 6,902,793.

(30) Foreign Application Priority Data

Jun. 8, 2001 (JP) ................................. 2001-174866

(51) Int. Cl.
  B29C 49/08 (2006.01)
  B29C 65/00 (2006.01)
  D04H 1/00 (2006.01)
  B32B 3/28 (2006.01)
(52) U.S. Cl. ..................... 264/288.4; 156/164; 442/328; 428/181

(58) Field of Classification Search ............... 264/288.4; 428/181; 442/328; 156/164
See application file for complete search history.

(56) References Cited

U.S. PATENT DOCUMENTS

| 3,386,130 | A | * | 6/1968 | Grunewald et al. ............. 425/86 |
| 4,102,720 | A | * | 7/1978 | Kaneko et al. ................... 156/78 |
| 4,211,743 | A | * | 7/1980 | Nauta et al. .................... 264/284 |
| 4,720,415 | A | * | 1/1988 | Vander Wielen et al. ..... 428/152 |
| 5,156,793 | A |   | 10/1992 | Buell et al. |
| 5,342,343 | A |   | 8/1994 | Kitaoka et al. |
| 5,529,830 | A |   | 6/1996 | Willman et al. |
| 5,681,302 | A |   | 10/1997 | Melbye et al. |
| 6,468,630 | B1 |   | 10/2002 | Mishima et al. |
| 6,610,039 | B1 | * | 8/2003 | Wilhelm et al. ......... 604/385.27 |

FOREIGN PATENT DOCUMENTS

EP 0 985 394 3/2000

* cited by examiner

Primary Examiner — Christina Johnson
Assistant Examiner — Michael Piery
(74) Attorney, Agent, or Firm — Brinks Hofer Gilson & Lione

(57) ABSTRACT

Here is disclosed a composite sheet comprising substantially non-stretchable nonwoven fabric sheets and a plurality of elastic members extending in a transverse direction and spaced one from another in a longitudinal direction by a given spacing wherein the elastic members are secured in a stretched state to the nonwoven fabric sheets. The composite sheet has a plurality of gathers formed by slightly undulated surface of the nonwoven fabric sheets and the elastic members and these gathers are substantially continuous in the longitudinal direction and arranged at substantially regular intervals in the transverse direction.

4 Claims, 10 Drawing Sheets

STRETCHABLE COMPOSITE SHEET AND PROCESS FOR FORMING THE SAME WITH A PLURALITY OF GATHERS

The present application is a divisional application of U.S. patent application Ser. No. 10/165,228, filed Jun. 7, 2002 now U.S. Pat. No. 6,902,793 which claims priority under 35 U.S.C. §119 to Japanese Patent Application No. 2001-174865, filed Jun. 8, 2001.

BACKGROUND OF THE INVENTION

This invention relates to a stretchable composite sheet and process for forming the same with a plurality of gathers.

A stretchable sheet of well known art is generally classified into a sheet which is perse elastically stretchable and a stretchable composite sheet comprising a substantially non-stretchable sheet member and a plurality of stretchable elastic members bonded in a stretched state to this substantially non-stretchable sheet member. An example of conventional stretchable composite sheets will be explained as follows with reference to a drawing in FIG. 10 of the accompanying drawings. In FIG. 10, a transverse direction is indicated by an arrow X and a longitudinal direction is indicated by an arrow Y.

A composite sheet 40 comprises a pair of substantially non-stretchable fibrous nonwoven fabric 41, 42 placed upon each other and a plurality of stretchable elastic members 43 each extending in the transverse direction and spaced one from another by a given spacing in the longitudinal direction. These elastic members 43 are interposed between layers of the nonwoven fabric 41, 42 and bonded in tension in the transverse direction to the layers of the nonwoven fabric 41, 42. The composite sheet 40 is formed with a plurality of irregularly shaped gathers 44 and wrinkles 45 as the elastic members 43 contract. In this composite sheet 40 of well known art, these irregularly shaped gathers 44 and wrinkles 45 are smoothed when the composite sheet 40 is placed under a tensile force in the transverse direction, and consequently the composite sheet 40 can be stretched in the transverse direction.

This composite sheet 40 includes regions 40a in which the gathers 44 and the wrinkles 45 are densely formed and regions 40b in which the gathers 44 and the wrinkles 45 are sparsely formed. In the regions in which many gathers 44 and wrinkles 45 are formed, a rate of elongation in the transverse direction in the composite sheet 40 presents a relatively high but correspondingly a layer force of elongation is high tensile force is required to smooth these gathers 44 and wrinkles 45. In the regions 40b in which the gathers 44 and the wrinkles 45 are sparsely formed, these gathers 44 and wrinkles 45 can be smoothed under a lower force of elongation than that in the regions 40a but the elongational rate of the composite sheet 40 in the transverse direction is lower than that in the regions 40a. Inconsequence, it is impossible to stretch this composite sheet 40 of well known art over its entire area in the longitudinal direction to the same length in the transverse direction by applying substantially uniform force of elongation.

SUMMARY OF THE INVENTION

This invention aims to provide a stretchable composite sheet improved so that the entire area thereof across a longitudinal direction may be stretched under a substantially uniform force of elongation in a transverse direction to a substantially same length without formation of a plurality of irregularly shaped wrinkles and/or gathers and a process for forming this composite sheet with a plurality of gathers.

According to this invention, there is provided a stretchable composite sheet having a first direction and a second direction intersecting the first direction, comprising substantially non-stretchable sheet members and a plurality of elastic members extending in the first direction spaced one from another in the second direction wherein the elastic members are secured in a stretched state to the sheet members.

The stretchable composite sheet further comprises a plurality of gathers formed by alternately undulated ups-and-downs of the sheet members, and the elastic members and the gathers are substantially continuous in the second direction and spaced one from another by substantially uniform spacing in the first direction.

The stretchable composite sheet according to this invention may be implemented also in such manners as described below:

The maximum height of the gathers from troughs to crests thereof as measured in regions containing the elastic members is lower than the maximum height from the troughs to the crests as measured in regions between respective pairs of the adjacent elastic members wherein the crests and the troughs of the gathers slightly undulate in the second direction.

Profiles connecting the crests and the troughs of the gathers show substantially circular arcs in the first direction.

The sheet members comprise a pair of fibrous nonwoven fabric sheets overlaid each other with the elastic members interposed between these nonwoven fabric sheets.

According to this invention, there is also provided a process for forming a plurality of gathers in a stretchable composite sheet, having a first direction and a second direction intersecting the first direction, comprising substantially non-stretchable sheet members and a plurality of elastic members extending in the first direction and spaced one from another by a given spacing in the second direction wherein the elastic members are secured in a stretched state to the sheet members so that the gathers are substantially continuous in the second direction and spaced one from another at substantially regular intervals in the first direction.

The process uses first and second rolls adapted to rotate in opposite directions wherein the second roll is provided on its peripheral surface with a plurality of elastic ridges extending in an axial direction of the second roll and spaced one from another by a given spacing in a circumferential direction so that a peripheral surface of the first roll and the elastic ridges of the second roll may be alternatingly contacted with and spaced away each other as these rolls rotate; the process comprises steps of feeding the composite sheet under a given extensional force in the first direction so as to be stretched in the first direction into a nip between the first and second rolls, holding the composite sheet between the peripheral surface of the first roll and the first elastic ridge of the elastic ridges of the second roll contacted with each other under a pressure, and, immediately before the peripheral surface of the first roll and the first elastic ridge of the second roll are spaced away from each other, the peripheral surface of the first roll and the second elastic ridge of the second roll lying immediately behind the first elastic ridge come in contact with each other under a pressure to hold the composite sheet; and in this way, the stress under which the composite sheet is placed is successively relaxed between each pair of the elastic ridges adjacent in the circumferential direction so that the sheet member may generate the gathers of which a trough is formed between each pair of the elastic ridges adjacent in the circumferential direction and crests on these elastic ridges.

The process according to this invention may be implemented also in such manners as described below:

Each pair of the elastic ridges adjacent in the circumferential direction have respective crests spaced from each other by a spacing of 6-60 mm.

The gathers are slightly undulated in the second direction.

The sheet member consists of two layers of fibrous nonwoven fabric sheets overlaid each other and the elastic members are interposed between these nonwoven fabric sheets.

DETAILED DESCRIPTION OF THE PREFERRED EMBODIMENTS

Details of the stretchable composite sheet and the process for making this stretchable composite sheet with a plurality of gathers both provided by this invention will be more fully understood from the description given hereunder in reference to the accompanying drawings.

Figure 1:
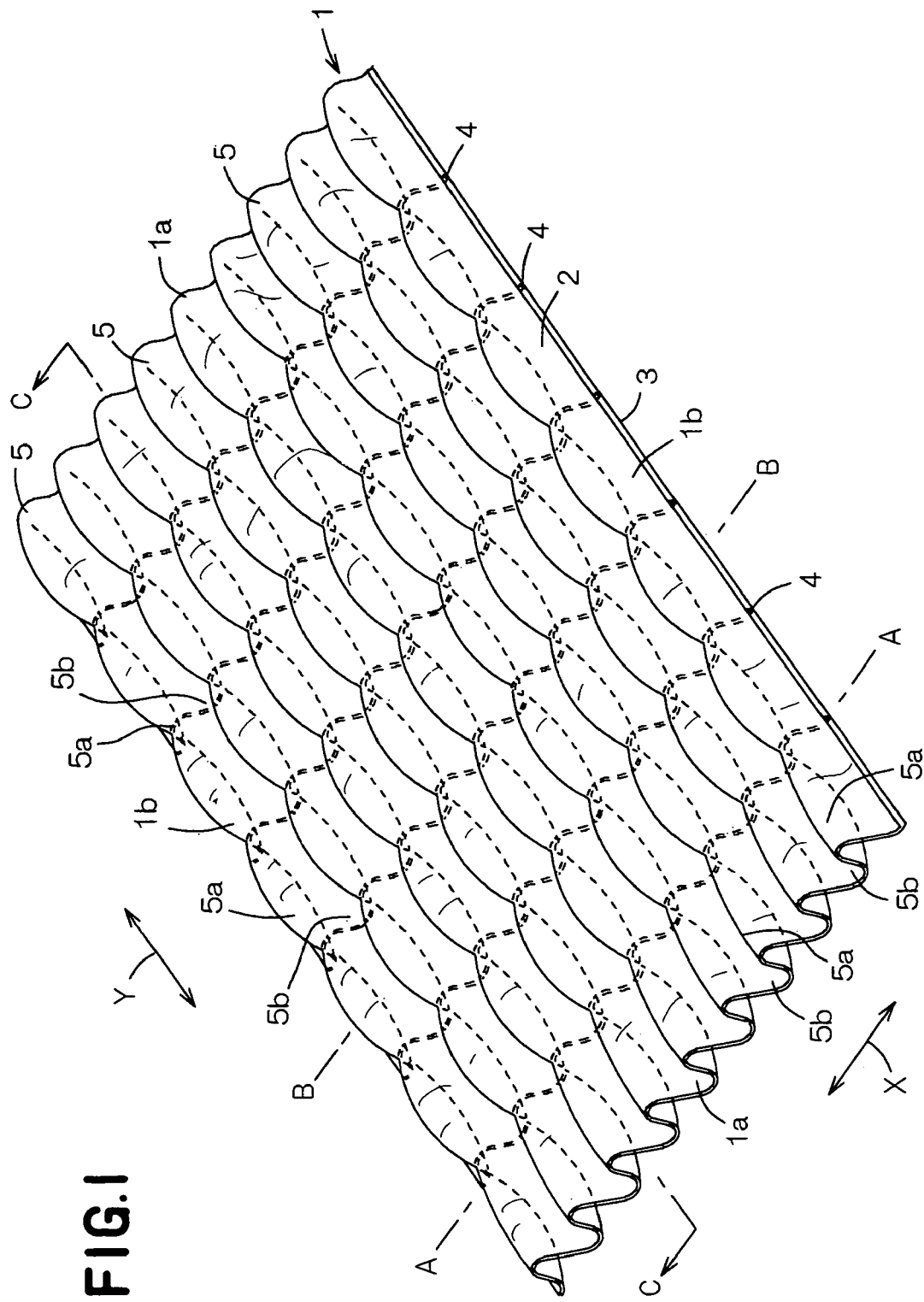
FIG. 1 is a perspective view of a stretchable composite sheet according to this invention.
Figure 2:
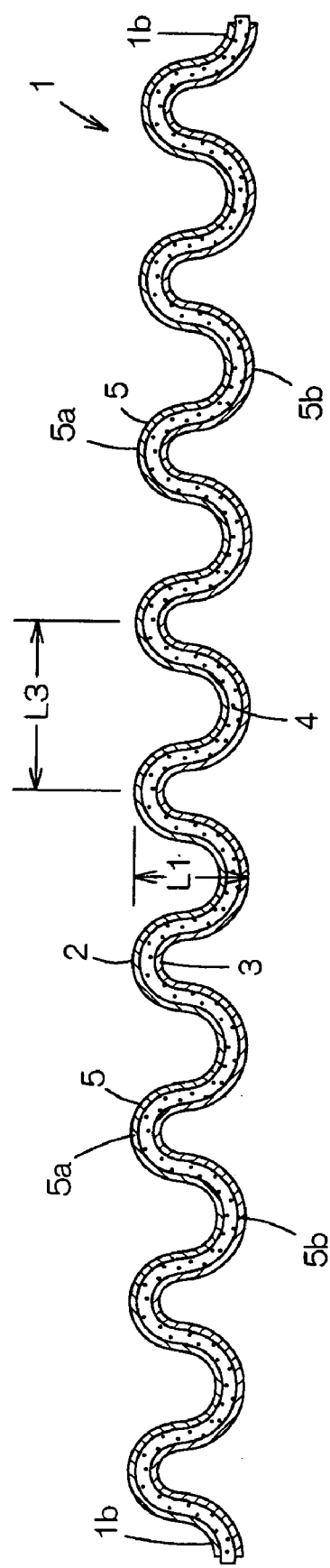
FIG. 2 is a cross-sectional view taken along a line A-A in FIG. 1.
Figure 3:
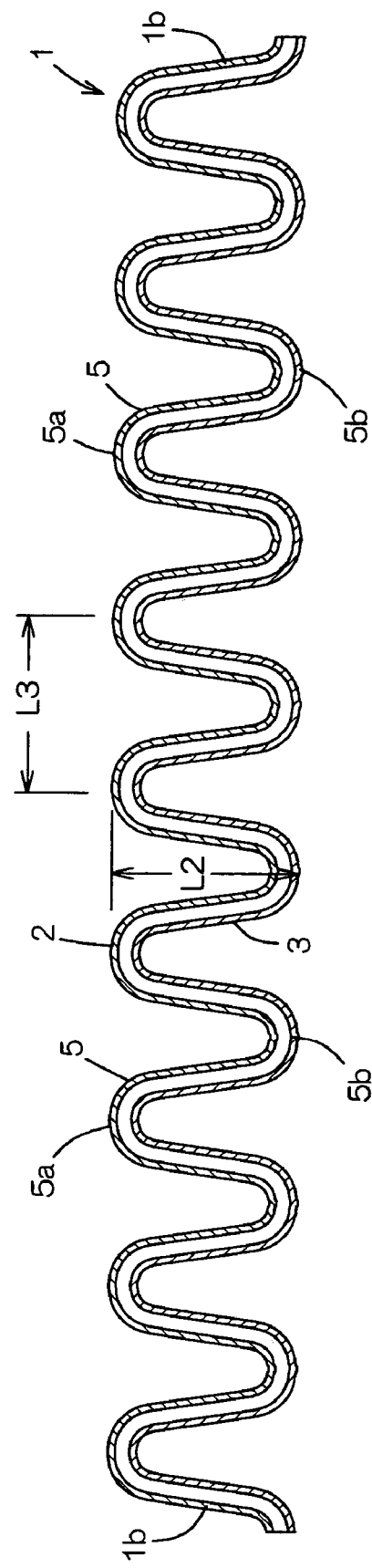
FIG. 3 is a cross-sectional view taken along a line B-B in FIG. 1.
Figure 4:
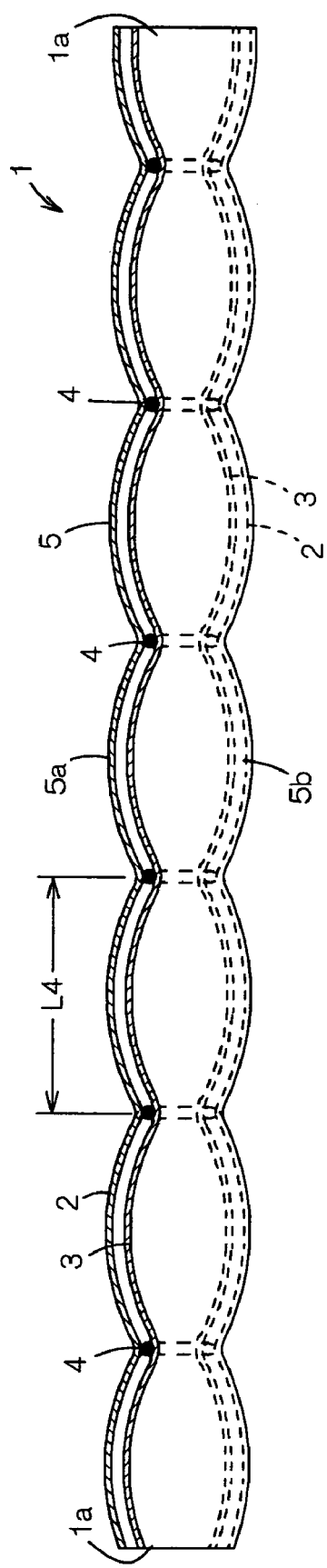
FIG. 4 is a cross-sectional view taken along a line C-C in FIG. 1.

FIG. 1 is a perspective view of the stretchable composite sheet 1 according to this invention, FIG. 2 is a cross-sectional view taken along a line A-A in FIG. 1, FIG. 3 is a cross-sectional view taken along a line B-B in FIG. 1 and FIG. 4 is a cross-sectional view taken along a line C - C in FIG. 1. In FIG. 1, a transverse direction is indicated by an arrow X and a longitudinal direction, orthogonal to X, is indicated by an arrow Y.

The composite sheet 1 comprises substantially nonstretchable fibrous nonwoven fabric sheets 2, 3 (sheet members) overlaid each other and a plurality of stretchable elastic members 4 extending in the transverse direction and spaced one from another by a given distance in the longitudinal direction. The composite sheet 1 is contoured by longitudinal opposite end edges 1a extending in the transverse direction and transversely opposite side edges 1b extending in the longitudinal direction. These elastic members 4 extend in parallel to the end edges 1a of the composite sheet 1. The elastic members 4 are interposed between the nonwoven fabric sheets 2, 3 and bonded in tension in the transverse direction to these nonwoven fabric sheets 2, 3. The composite sheet 1 is formed with a plurality of gathers 5 spaced one from another by the given spacing as the elastic member 4 contracts.

The gathers 5 are formed by alternately undulated ups-and downs of the surface of the nonwoven fabric sheets 2, 3 due to the contraction of the elastic members 4 in the transverse direction. Each row of the gathers 5 is extending in the longitudinal direction continuously and rather rectilinearly at regular intervals in the transverse direction. The gathers 5 have crests 5a and troughs 5b both of which extend rather rectilinearly in the longitudinal direction and show circular arcs in the transverse direction.

The maximum height L1 of the gathers from the troughs 5b to the crests 5a as measured in regions containing the elastic members 4 is less than the maximum height L2 from the troughs 5b to the crests 5a as measured in regions between respective pairs of the adjacent elastic members 4. Thus, alternately appearing ups and downs of the crests 5a and the troughs 5b of the gathers 5 make the composite sheet 1 slightly undulate also in the longitudinal direction.

The spacing distance L3 between adjacent crests 5a of the gathers 5 in the transverse direction is preferably in a range of 3-30 mm. If the spacing distance L3 is less than 3 mm, the number of the gathers 5 arranged in the transverse direction would be excessively large and the number of the gathers 5 in the transverse direction would be correspondingly increased. As a result, stiffness of the composite sheet 1 in the transverse direction would be extremely increased and flexibility of the composite sheet 1 would be reduced. If the spacing distance L3 exceeds 30 mm, on the contrary, the gathers 5 would be readily collapsed.

The maximum height L1 from the troughs 5b to the crests 5a of the gathers 5 containing the elastic members 4 is preferably in a range of 1-3 mm and the maximum height L2 from the trough 5b to the crest 5a of the gather 5 defined in regions between each pair of the adjacent elastic members 4 is preferably in a range of 3-10 mm. If the maximum height L1 is less than 1 mm, it is apprehended that none of the gathers 5 continuously extending in the longitudinal direction might be formed. If the maximum height L2 exceeds 10 mm, the gathers 5 would be bulky and reduce a good feeling of touch of the composite sheet 1.

The spacing distance L4 between adjacent elastic members in the longitudinal direction is preferably in a range of 3-30 mm. If the spacing distance L4 is less than 3 mm, the composite sheet 1 would be formed with too many fine wrinkles and it would be impossible to form the composite sheet 1 with the desired gathers 5 extending in the longitudinal direction continuously and rather rectilinearly. If the spacing distance L4 exceeds 30 mm, on the contrary, it would be impossible to form the composite sheet 1 with the gathers 5 fully extending across each pair of the adjacent elastic members 4.

A shrinkage rate in the transverse direction per unit length of the composite sheet 1 in regions each containing the elastic member 4 is preferably in a range of 40-80%. If the shrinkage rate exceeds 80%, the composite sheet 1 would be formed with so many irregularly shaped gathers 5 and it would be impossible to form the composite sheet 1 with the desired gathers 5 continuously and rather rectilinearly extending in the longitudinal direction. If the shrinkage rate is less than 40%, on the contrary, it is apprehended that the composite sheet 1 could not be formed with the gathers 5 themselves.

Figure 10:
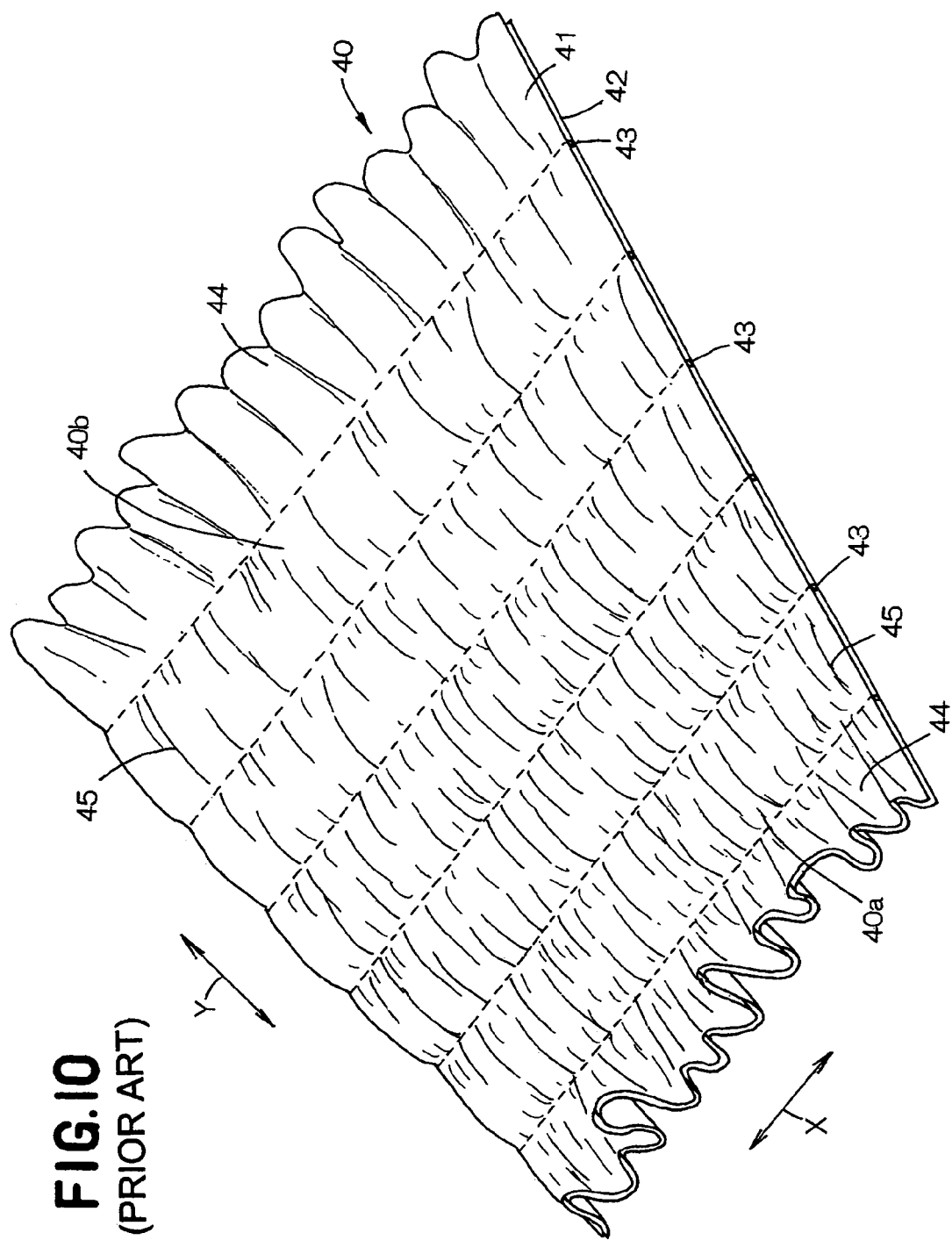
FIG. 10 is a perspective view showing an example of the conventional stretchable composite sheets.

As an extensional force is applied to the composite sheet 1 in the transverse direction, the gathers 5 are smoothed out in the transverse direction so that the composite sheet 1 is substantially flattened and stretched in the transverse direction. Upon removal of this force in the transverse direction, the composite sheet 1 contracts itself to regenerate the gathers 5. Unlike the conventional composite sheet as shown in FIG. 10 in which the gathers and/or wrinkles are irregularly formed, the composite sheet 1 according to this invention can be stretched almost uniformly to the same extent in the transverse direction over the entire region in the longitudinal direction by a substantially uniform force of elongation.

The gathers 5 continuously and rather rectilinearly extend in the longitudinal direction and are arranged in the transverse direction substantially at regular intervals. Such unique arrangement is effective to prevent any portion of the gathers 5 from being angularly bent and these gathers 5 play a role like a cushion so as to improve a feeling of touch of the composite sheet 1.

Figure 5:
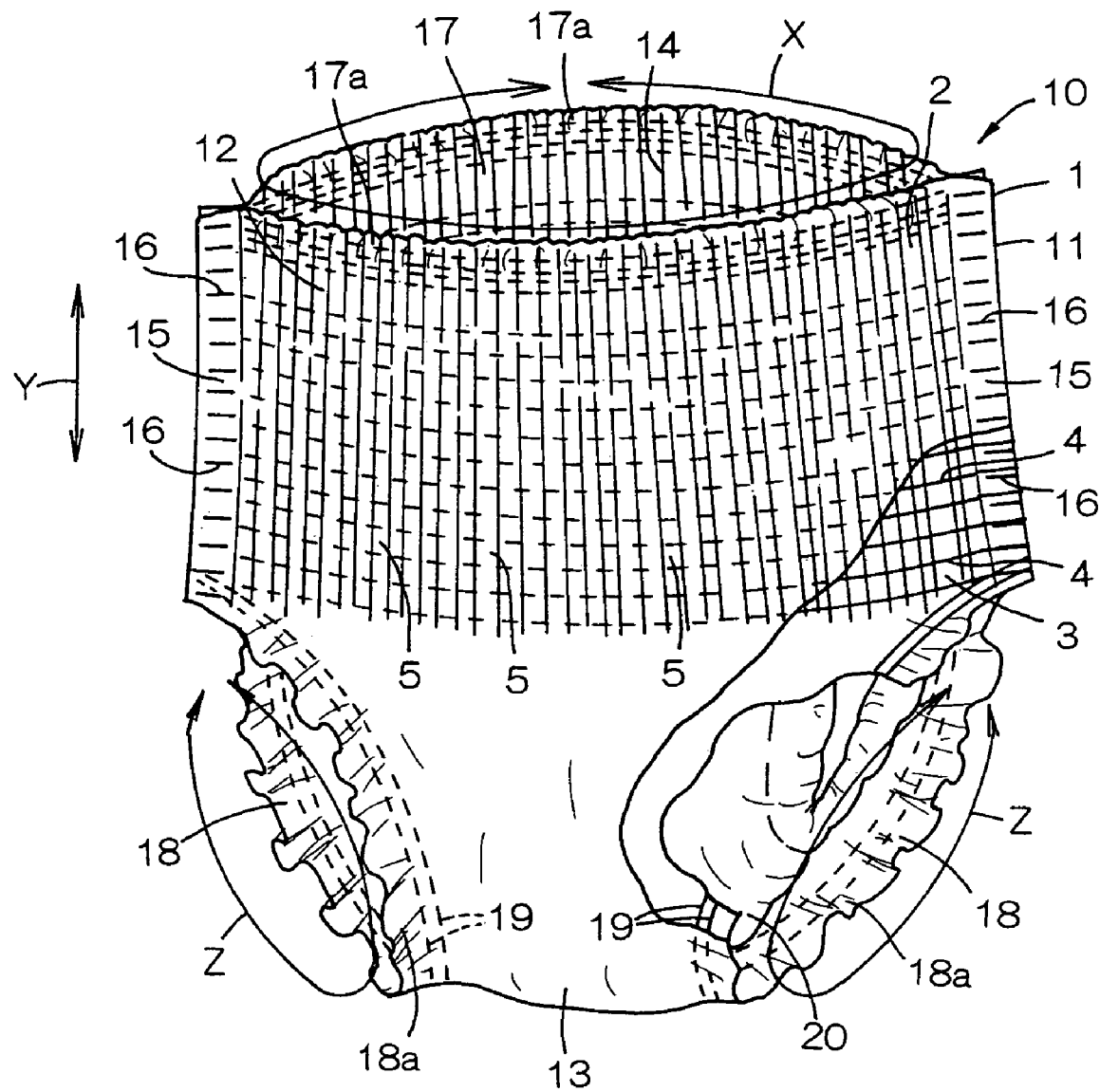
FIG. 5 is a partially cutaway perspective view showing a pants-type disposable diaper using the composite sheet.
Figure 6:
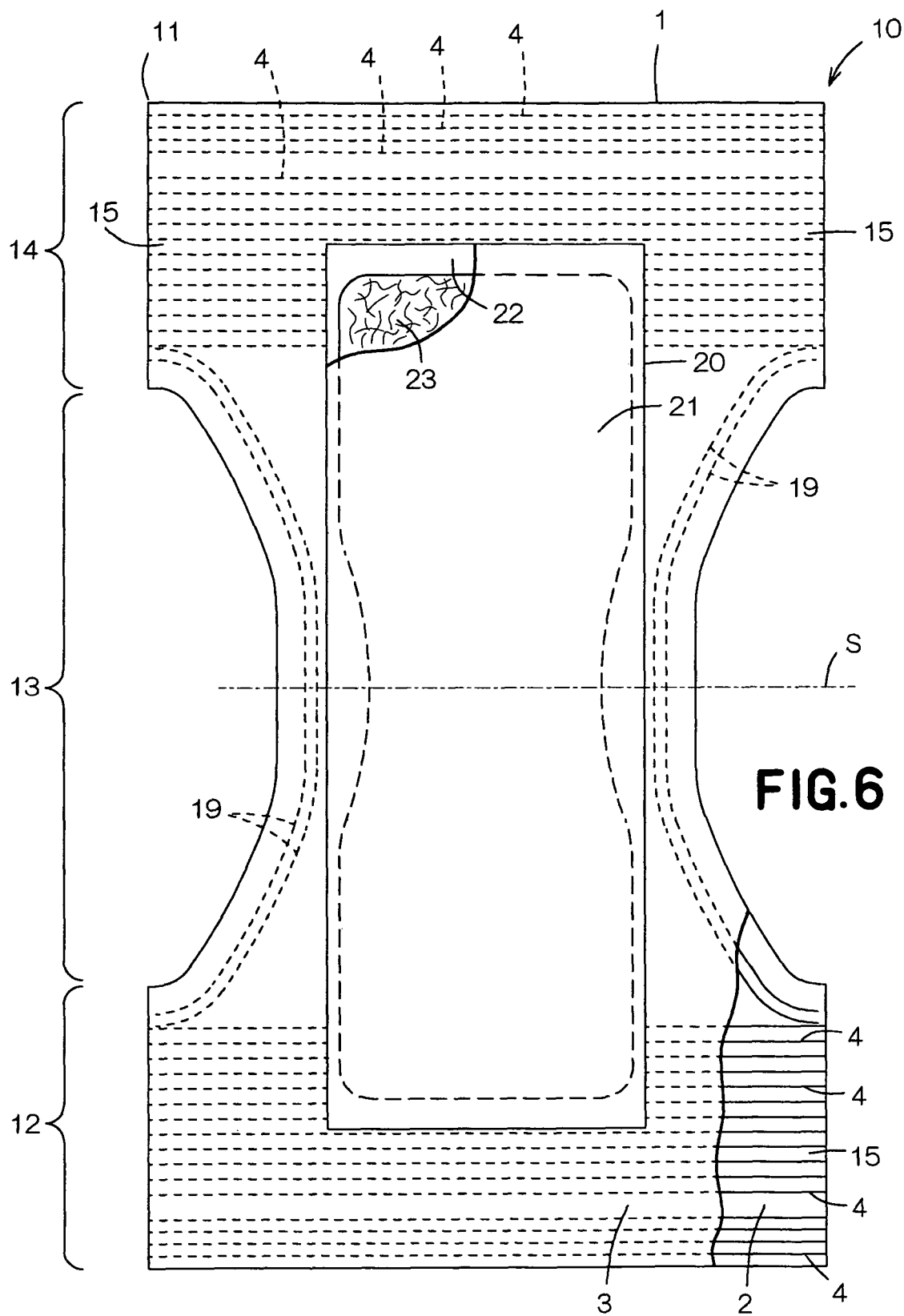
FIG. 6 is a partially cutaway plan view showing the diaper before shaped in pants-type.

FIG. 5 is a partially cutaway perspective view showing a pants-type disposable diaper 10 using the composite sheet 1 and FIG. 6 is a partially cutaway plan view showing the diaper 10 before shaped into a pants-type one. In FIG. 5, a waist-surrounding direction is indicated by an arrow X, a longitudinal direction is indicated by an arrow Y and a thigh-surrounding direction is indicated by an arrow Z.

The diaper 10 basically comprises a basic body 11 of the diaper and a liquid-absorbent pad 20. The basic body 11 is composed of front and rear waist regions 12, 14 opposed to each other and a crotch region 13 extending between these waist regions 12, 14. The basic body 11 is formed by the composite sheet 1 shown in FIG. 1.

The front and rear waist regions 12, 14 are overlaid along transversely opposite side edges 15 of these waist regions 12, 14 and joined by means of a plurality of heat-sealing lines 16 arranged intermittently in the longitudinal direction along these transverse opposite side edges 15. The basic body 11 is provided with a waist-hole 17 and a pair of leg-holes 18 below the waist-hole 17.

The elastic members 4 are arranged at a given spacing in the longitudinal direction between a peripheral edge 17a of the waist-hole 17 and the crotch region 13. The elastic members 4 extending substantially in parallel to the peripheral edge 17a of the waist-hole 17. The elastic members 4 are interposed between nonwoven fabric sheets 2, 3 forming the basic body 11 and secured in tension in the waist-surrounding direction to these nonwoven fabric sheets 2, 3.

The front and rear waist regions 12, 14 of the basic body 11 are formed with a plurality of gathers 5 arranged at a given spacing from each other in the waist-surrounding direction. These gathers 5 extend continuously and rather rectilinearly in the longitudinal direction from the waist-hole 17 toward the crotch region 13 and arranged substantially at regular intervals.

A plurality of elastic members 19 are secured in a stretched state to peripheral edges 18a of the respective leg-holes 18. These elastic members 19 are interposed between the nonwoven fabric sheets 2, 3 and secured in tension in the thigh-surrounding direction to the respective nonwoven fabric sheets 2, 3.

The liquid-absorbent pad 20 comprises a liquid-pervious topsheet 21 facing a wearer's skin, a liquid-impervious backsheet 22 facing away from the wearer's skin and a liquid-absorbent core 23 interposed between these sheets 21, 22 and bonded to the inner surface of at least one of these sheets 21, 22.

The liquid-absorbent pad 20 extends across the crotch region 13 into the front and rear waist regions 12, 14 of the basic body 11. The liquid-absorbent pad 20 is partially bonded to the front and rear waist regions 12, 14 of the basic body 11 by means of hot melt adhesive (not shown).

The topsheet 21 may be formed by fibrous nonwoven fabric or plastic film having a plurality of micro pores. The backsheet 22 may be formed by a material selected from a group of materials consisting of hydrophobic fibrous nonwoven fabric, breathable but liquid impervious plastic film, composite nonwoven fabric comprising hydrophobic fibrous nonwoven fabric layers placed one upon another, and a composite sheet comprising hydrophobic fibrous nonwoven fabric and breathable but liquid-impervious plastic film placed upon each other. The topsheet 21 and the backsheet 22 are bonded together along peripheral edges of these sheets 21, 22 extending outward beyond a peripheral edge of the core 23.

The core 23 is a mixture of fluff pulp and super-absorbent polymer particles or a mixture of fluff pulp, super-absorbent polymer particles and thermoplastic synthetic resin fiber compressed to a desired thickness. The core 23 is preferably covered with and joined to tissue paper in order to prevent the core 15, 20 from losing their shapes and/or to prevent polymer particles from falling off. The polymer particles may be selected from a group of materials consisting of starch-based, cellulose-based and synthetic polymer.

To obtain the diaper 10 of FIG. 5 from a state shown in FIG. 6 as a plan view, the basic body 11 may be folded back along a transverse center line S extending across the crotch region 13 with the liquid-absorbent pad 20 inside to put the front and rear waist regions 12, 14 flat together and then to bond these waist regions together along the transversely opposite side edges 15 thereof.

With the diaper 10 being worn, the troughs 5b of the gathers 5 formed in the basic body 11 come in contact with a wearer's torso and the crests 5a of the gathers 5 are spaced from the wearer's torso. Gaps are formed between the crests 5a of the gathers 5 and the wearer's torso and extend continuously and rather rectilinearly between the crotch region 13 and the waist-hole 17 in the longitudinal direction. Such unique arrangement allows stuffy moisture generated within the diaper 10 to escape from the waist-hole 17 through the respective gaps.

The gathers 5 continuously and rather rectilinearly extend between the crotch region 13 and the waist-hole 17 and are arranged substantially at regular intervals. Therefore, the gathers 5 contacting the wearer's torso are not apt to be angularly bent and thereby to locally compress the wearer's skin. Furthermore, these gathers 5 function as a cushion to improve a feeling of touch of the diaper 10 when it is worn.

As both the crests 5a and the troughs 5b of the respective gathers 5 extending in the waist-surrounding direction draw shapes of circular arcs, there is no anxiety that the troughs 5b of the gathers 5 might give the wearer an uncomfortable irritation even these troughs 5b come in contact with the wearer's torso as the conventional article having somewhat pointed crests and/or troughs of gathers has been the case.

Figure 7:
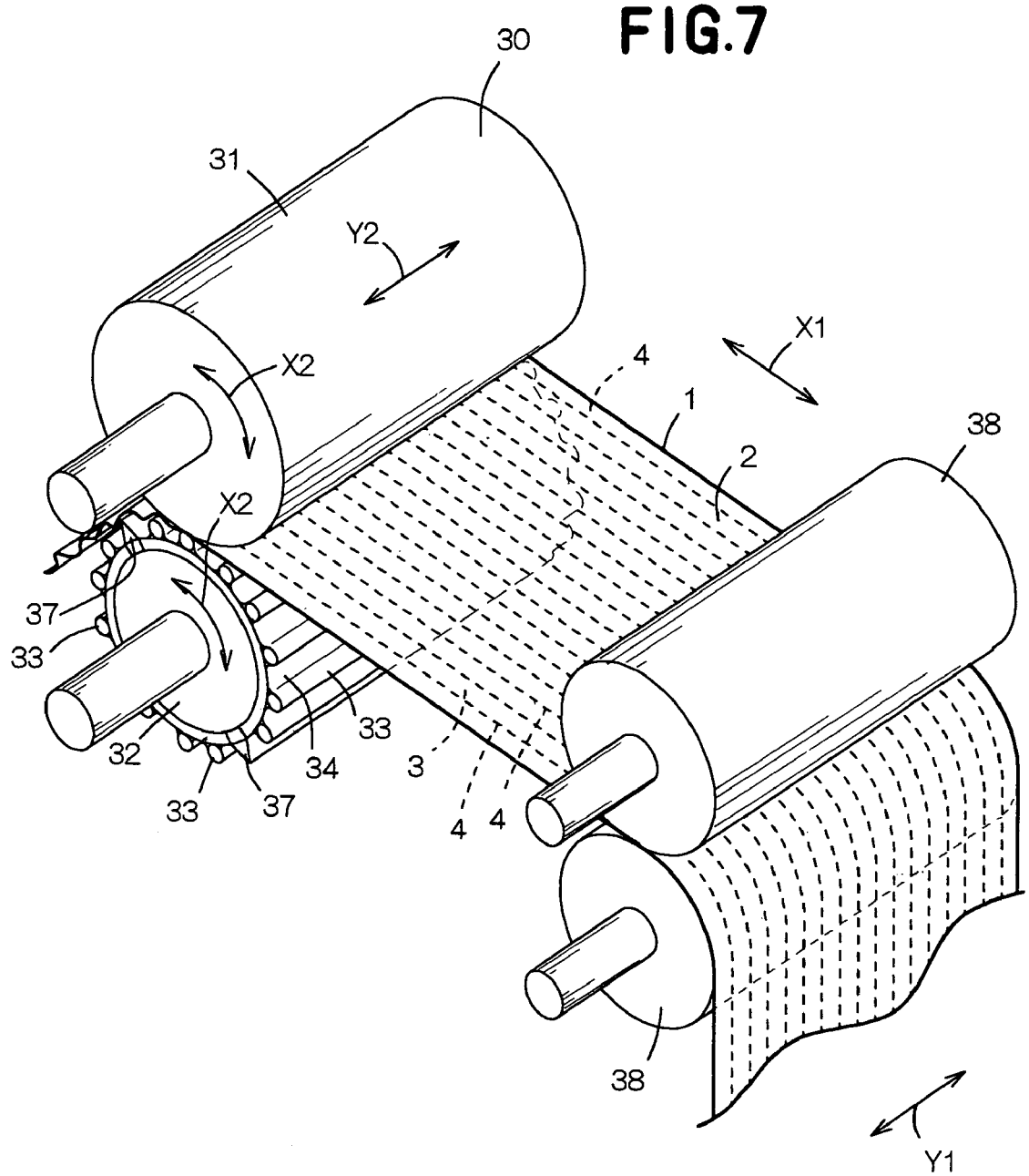
FIG. 7 is a perspective view showing a flat roll cooperating with an embossing roll.
Figure 8:
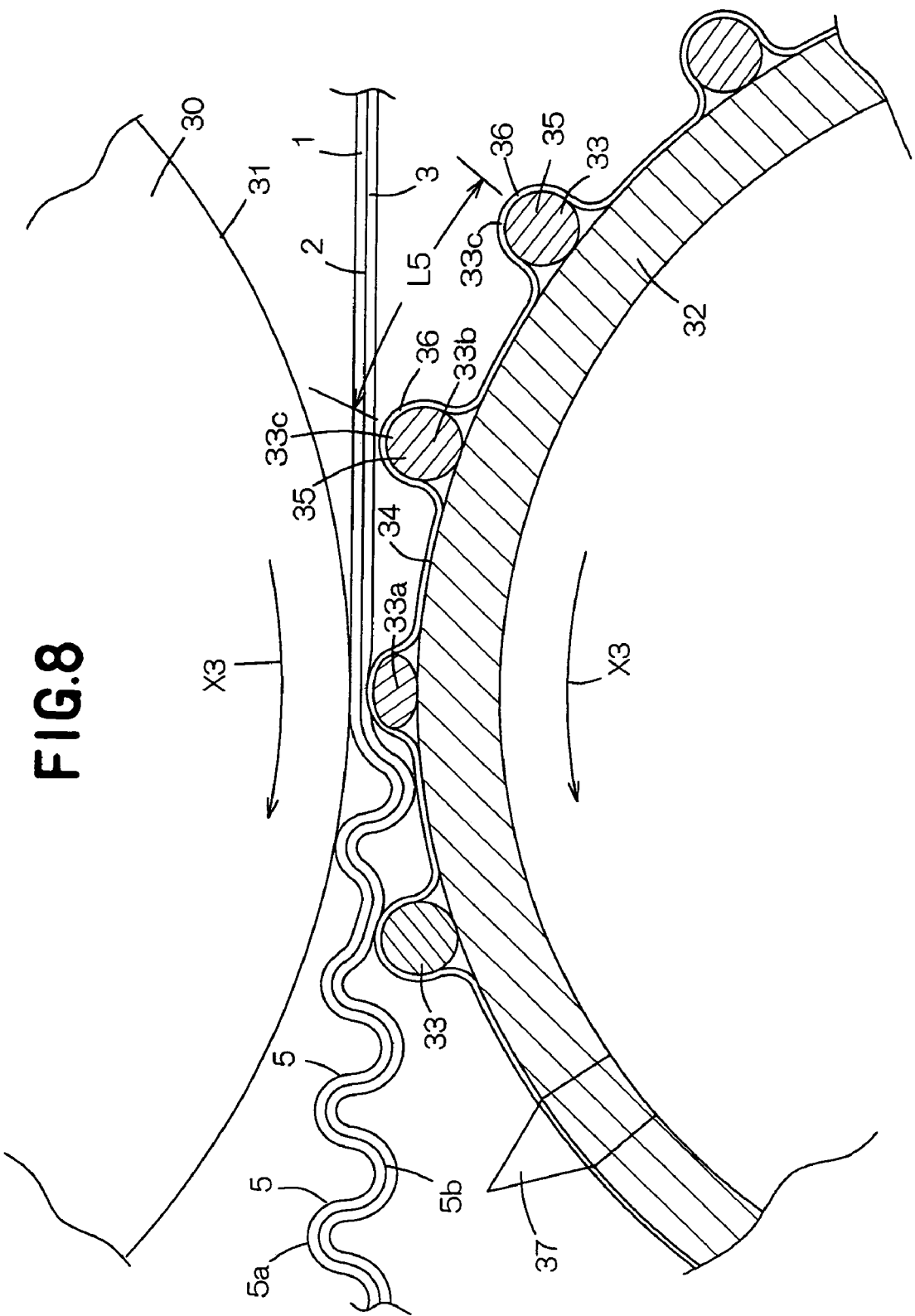
FIG. 8 is a fragmentary side view showing these rolls as the composite sheet runs through between these rolls.
Figure 9:
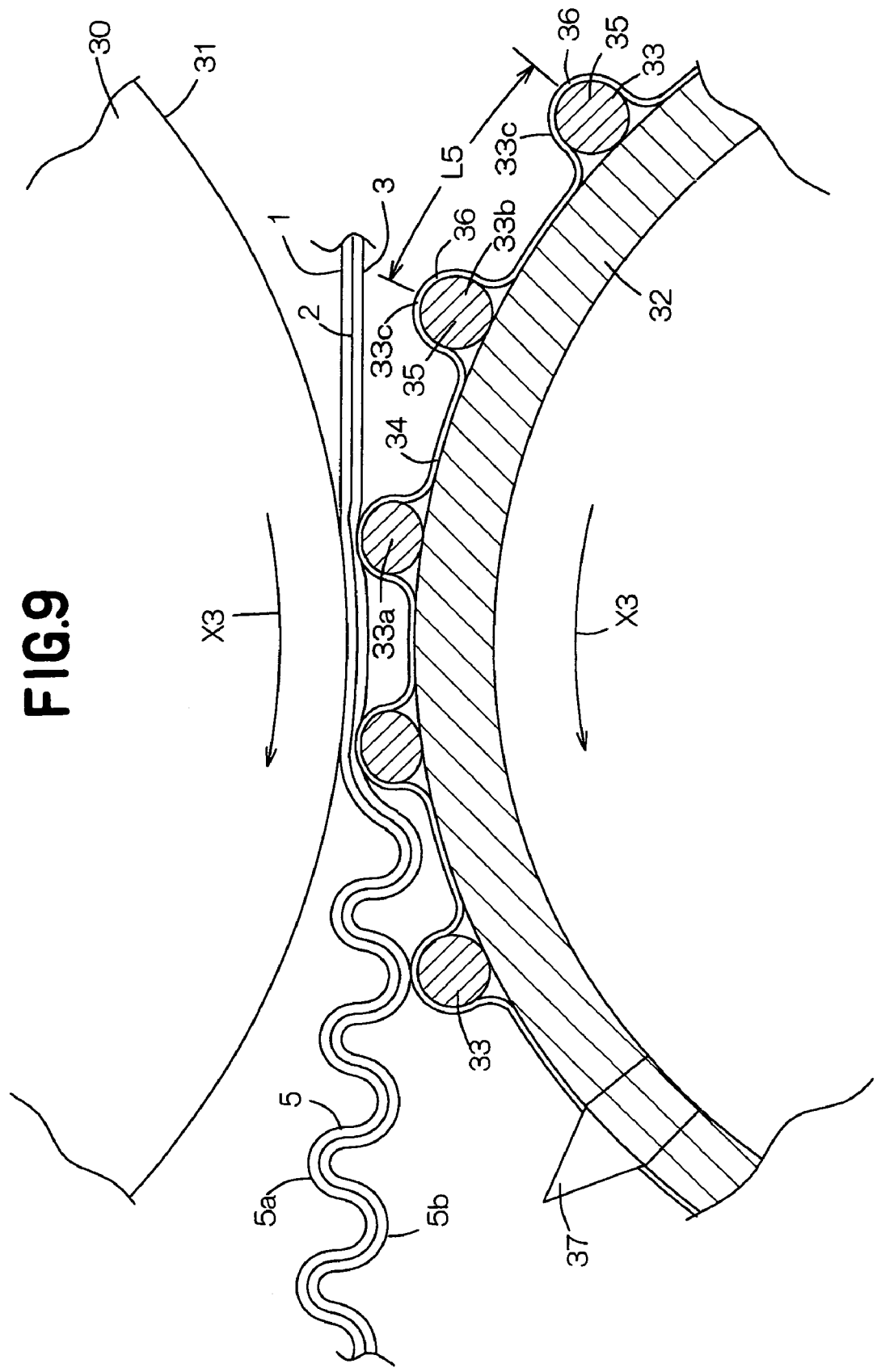
FIG. 9 is a fragmentary side view showing these rolls as the composite sheet runs through between these rolls.

FIG. 7 is a perspective view showing a flat roll 30 and an embossing roll 32 used in a process for forming the composite sheet 1 with the gathers 5, and FIGS. 8, 9 are fragmentary side views showing these rolls 30, 32 as the composite sheet 1 runs through gaps between these rolls 30, 32. In these figures, a transverse direction is indicated by an arrow X1, a longitudinal direction is indicated by an arrow Y1, a circumferential direction of the rolls 30, 32 is indicated by an arrow X2 and an axial direction of the rolls 30, 32 is indicated by Y2.

The process for making the composite sheet 1 with the gathers 5 uses the flat roll 30 (first roll) having a peripheral surface 31 which is substantially flat and the embossing roll 32 (second roll) having a peripheral surface 34 formed with a plurality of elastic ridges 33.

The elastic ridges 33 extend on the peripheral surface 34 of the embossing roll 32 in the axial direction spaced one from another by a given spacing in the circumferential direction. Each of these elastic ridges 33 is formed by a substantially cylindrical elastic member 35 extending in the axial direction. The peripheral surface 34 of the embossing roll 32 and those elastic members 35 are covered with plastic film 36. The embossing roll 32 includes, in addition to those elastic ridges 33, a pair of cutters 37 extending in the axial direction. The pair of cutters 37 are attached to the peripheral surface 34 of the embossing roll 32 so as to be spaced from each other in the circumferential direction by an angle of approximately 180°.

As will be apparent from FIGS. 8 and 9, the peripheral surface 31 of the flat roll 30 and the elastic ridges 33 of the embossing roll 32 are repeatedly touched with and spaced away from each other as these rolls 30, 32 rotate in the direction indicated by the arrow X3 when the composite sheet 1 is not fed.

The composite sheet 1 comprises substantially non-stretchable fibrous nonwoven fabric sheets 2, 3 (sheet member) which are overlaid each other and continuous in the transverse direction and a plurality of stretchable elastic members 4 extending in the transverse direction spacing one from another by a given distance in the longitudinal direction. These elastic members 4 are interposed between the nonwoven fabric sheets 2, 3 and bonded in tension in the transverse direction to these nonwoven fabric sheets 2, 3.

The composite sheet 1 is invited to a gap between a pair of nip rolls 38 to be up-taken by the flap roll 30 and the embossing roll 30 and the embossing roll 32. Between the nip rolls 38 and the rolls 30, 32, which are working as up-take roils, a definite amount of an extensional stress is applied to the composite sheet 1 in its transverse direction.

As is shown in FIG. 8, the composite sheet 1 advanced to the rolls 30,32 is held by a compressive force generated in a gap between an elastic ridge 33a, which is one of the elastic ridges 33, and the peripheral surface 31 of the flat roll 30. Then, as is shown in FIG. 9, immediately before the composite sheet 1 is leaving the gap between the ridge 33a and the peripheral surface 31 of the flat roll 30, another elastic ridge 33b, which is positioned next to the ridge 33a on the peripheral surface of the flat roll 30, comes round to press the composite sheet 1 to the rolls 30 and 32. Therefore, the composite sheet 1 is held by two elastic ridges, 33a, and 33b at two points between the rolls 30 and 32.

The extensional stress stored in the composite sheet 1 is relieved immediately after the composite sheet 1 has been spaced away from one of the elastic ridges 33 arranged in the circumferential direction of the embossing roll 32. In the composite sheet 1, upon leaving the gap between the flat roll 30 and the embossing roll 32, the nonwoven fabric sheets 2,3 and the elastic members 4 contract themselves in the transverse direction with substantially a uniform shrinkage rate over the entire region in the longitudinal direction. In this process, slightly undulated ups and downs of the surface of the nonwoven fabric sheets 2, 3 and the elastic members 4 extending in the circumferential direction between the adjacent elastic ridges 33 gives the composite sheet 1 a row of gathers 5 between the adjacent elastic ridges 33. In this process, the composite sheet 1 is cut off in the lolngitudinal direction with the cutter 37 attached to the embossing roll 32 every 180 degrees of rotation by the embossing roll 32.

On the embossing roll 32, each pair of the elastic ridges 33 being adjacent in the circumferential direction have respective crests 33c which are spaced from each other by a spacing L5 of 6-60 mm. The spacing L5 is preferably in a range of 6-30 mm. If the spacing L5 is less than 6 mm, it would be difficult for the portions of the nonwoven fabric sheets 2, 3 and the elastic members 4 extending these adjacent elastic ridges 33 to undulate and, in consequence, to form the composite sheet 1 with the gather 5 continuously and rather rectilinearly extending in the longitudinal direction. If the spacing L5 exceeds 60 mm, on the contrary, two or more gathers may be formed between these adjacent two elastic ridges 33 and, in consequence, the composite sheet 1 may be formed with irregular gathers 5.

This process enables the composite sheet 1 to be formed with a plurality of the gathers 5 extending in the longitudinal direction and arranged in the transverse direction at substantially regular intervals merely by feeding the composite sheet 1 under the given extensional force in the transverse direction into the nip between the flat roll 30 and the embossing roll 32.

The nonwoven fabric layers 2, 3 forming the composite sheet 1 may be selected from any of those made by spun lace-, needle punch-, melt blown-, spun bond-, chemical bond- and air through-processes.

A component fiber of the nonwoven fabric layers 2, 3 may be selected from a group of materials consisting of polyolefine-based, polyester-based and polyamide-based fibers and core-sheath-type or side-by-side-type conjugated fiber of polyethylene/polypropylene or polyester.

It is also possible to use a composite sheet consisting of two or more layers of breathable but liquid-impervious plastic film placed one on another or a composite sheet consisting of hydrophobic fibrous nonwoven fabric and breathable but liquid-impervious plastic film placed upon each other.

Natural rubber or synthetic rubber may be used as a material for both the elastic members and the elastic members 35. The elastic members 4 are preferably to be thread-like or band-like. The nonwoven fabric layers 2, 3 may be bonded to each other by means of the elastic members 4 or, in addition, sheets nonwoven fabric layers 2, 3 themselves may be also partially bonded to each other.

The nonwoven fabric sheets 2, 3 are bonded to the elastic members 4 preferably using hot melt adhesive selectively in a spiral pattern or a spray pattern of hot melt adhesive. In order that the elastic members 4 may be reliably bonded to the nonwoven fabric sheet 2, 3, a percentage of an adhesive coated area is preferably in a range from 20% to 80% to a total surface area of the elastic members 4. If the percentage of the adhesive coated area is less than 20%, it is apprehended that the elastic members 4 might fall off from the nonwoven fabric layers 2, 3. If the percentage of the adhesive coated area exceeds 80%, on the contrary, contraction of the elastic members 4 would be obstructed by the presence of the adhesive.

The stretchable composite sheet according to this invention is primarily characterized in that the gathers continuously extend in the longitudinal direction and are arranged substantially at regular intervals in the transverse direction. Such unique arrangement enables the entire area of the composite sheet in the longitudinal direction to be stretched under substantially uniform tensile force to substantially the same extent. With this composite sheet, the gathers are not apt to be partially and angularly bent and these gathers function as a cushion to improve a feeling of the touch of the composite sheet. With this composite sheet, both the crests and the troughs of the respective gathers delineate substantially circular arcs in the transverse direction. Therefore, the composite sheet offers the touch more comfortable than the conventional composite sheet having somewhat pointed crests and/or troughs of gathers can offer.

The process according to this invention enables to make with ease a composite sheet with a plurality of the gathers extending in the longitudinal direction and spacing in the transverse direction at substantially regular intervals merely by feeding the composite sheet under a given tensile force in the transverse direction into the nip between the first roll and the second roll.

This stretchable composite sheet is suitable as a stock material for various wearing articles such as a disposable diaper and a diaper cover.

What is claimed is:

1. A process for forming a plurality of gathers in a stretchable composite sheet having a first direction and a second direction intersecting said first direction, comprising substantially non-stretchable sheet members and a plurality of elastic members each of the plurality of elastic members extending in said first direction and each of the plurality of elastic members being spaced one from another by a given spacing in said second direction wherein said elastic members being secured in a stretched state to said sheet members so that said gathers being substantially continuous in said second direction and spaced one from another at substantially regular intervals in said first direction, said process further comprising: a process using first and second rolls adapted to rotate in opposite directions wherein said second roll is provided on its peripheral surface with a plurality of discrete spaced apart elastic ridges that extend in an axial direction on a peripheral surface of said second roll and are spaced apart from one another by a given spacing in a circumferential direction on said peripheral surface of said second roll so that a peripheral surface of said first roll and of said elastic ridges of said second roll may be alternatingly contacted with and spaced away from each other as these rolls rotate; a process comprising the steps of feeding said composite sheet placed under a given extensional force in said second direction so as to be stretched in said second direction into a nip between said first and second rolls, holding said composite sheet between the peripheral surface of said first roll and a first elastic ridge of said elastic ridges of said second roll contacted with each other under a pressure, and, immediately before the peripheral surface of said first roll and the first elastic ridge of said second roll being spaced away from each other, the peripheral surface of said first roll and the second elastic ridge of said second roll lying immediately behind said first elastic ridge coming in contact with each other under a pressure to hold said composite sheet so as to stress said composite sheet in a space between the first and second elastic ridges; and the stress under which said composite sheet is placed being successively relaxed between each pair of the elastic ridges adjacent in said circumferential direction so that said sheet member may generate said gathers of which a trough is formed between each pair of the elastic ridges adjacent in said circumferential direction and crests on these elastic ridges, said process forming a plurality of gathers formed by alternately undulated ups-and-downs in a transverse direction and alternating crests and troughs which extend in a longitudinal direction of said sheet members.

2. The process according to claim 1, wherein each pair of said elastic ridges adjacent in said circumferential direction have respective crests spaced from each other by a spacing of 6-60 mm.

3. The process according to claim 1, wherein said gathers are slightly undulated in said first direction.

4. The process according to claim 1, wherein said sheet members consists of two fibrous nonwoven fabric sheets overlaid each other and said elastic members are interposed between these nonwoven fabric sheets.

* * * * *